United States Patent [19]

Pohndorf

[11] Patent Number: 5,613,953
[45] Date of Patent: Mar. 25, 1997

[54] SHEATH INTRODUCER WITH VALVE THAT SPLITS

[75] Inventor: Peter J. Pohndorf, Stillwater, Minn.

[73] Assignee: Medtronic, Inc., Minneapolis, Minn.

[21] Appl. No.: 638,039

[22] Filed: Apr. 26, 1996

[51] Int. Cl.$^6$ ........................................... A61M 5/178
[52] U.S. Cl. ............................ 604/165; 606/1; 604/160; 604/161
[58] Field of Search .................................. 606/108, 181, 606/182; 604/165, 161, 160

[56] References Cited

U.S. PATENT DOCUMENTS

| | | | |
|---|---|---|---|
| 4,627,841 | 12/1986 | Dorr | 604/165 |
| 4,702,735 | 10/1987 | Luther et al. | 604/165 |
| 4,834,708 | 5/1989 | Pillari | 604/165 |
| 5,336,191 | 8/1994 | Davis et al. | 604/165 |
| 5,397,311 | 3/1995 | Walker et al. | 604/160 |

*Primary Examiner*—Sam Rimell
*Assistant Examiner*—Justine Yu
*Attorney, Agent, or Firm*—Michael J. Jaro; Harold R. Patton

[57] ABSTRACT

A transvenous lead introducer having an integral mechanical valve assembly which includes opposed comating valve members that are operated by opposed handles. The handles and the valves are joined by rotatable link assemblies and are normally biased in a closed position by integrally formed bias springs.

9 Claims, 4 Drawing Sheets

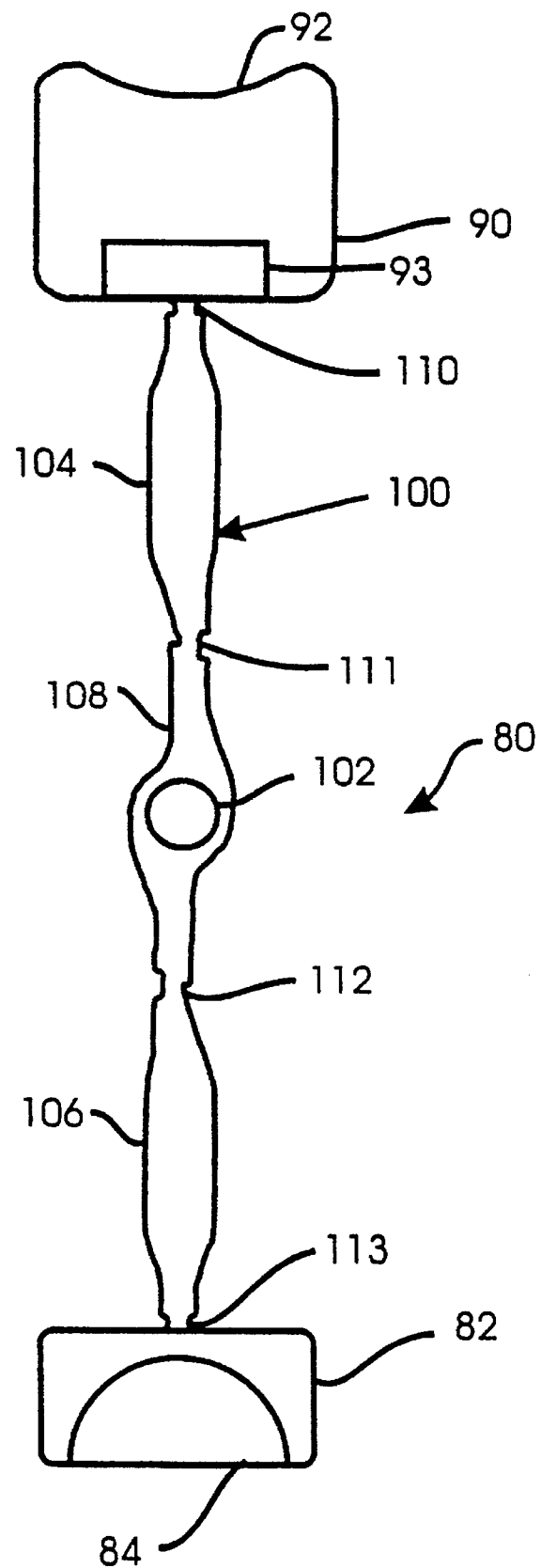

SHEATH INTRODUCER WITH VALVE THAT SPLITS

BACKGROUND OF THE INVENTION

1. Field of the Invention

This invention relates to an instrument for facilitating the introduction of transvenous leads into a human body, and more particular relates to valves for use in such an instrument.

2. Description of the Related Art

The use of electrically conducive transvenous lead, particularly cardiac pacing leads, is well known in the medical field. Many different methods and tools have been proposed in the prior art for allowing such leads to be introduced into the patient's subclavian vein via a relatively small incision. Often, medical device manufacturers may provide an introducer set to be used by doctors in implanting pacing leads.

A common feature of any method for introducing a lead into a patient's blood vessel is that a hollow, tubular instrument is required to provide a temporary passage or conduit into the blood vessel, though which the lead may be slid to enter the blood vessel. Such a conduit also allows blood to escape from the blood vessel, and may allow air to enter the blood stream, possibly leading to embolic complications.

In addition to the potential adverse clinical effects of leakage of blood and air through an introducer sheath, the flow of blood out of an introducer sheath is likely to make the physician's task more difficult, and may encourage the physician to perform the introduction procedure more hastily. This, in turn, can increase the tension associated with the introduction procedure, and the risk that mistakes will be made.

In the prior art, it is commonly suggested that the physician can prevent (or at least restrict) the flow of blood out of an introducer sleeve while the pacing lead is being prepared for introduction into the vein by placing his or her thumb over the exposed end of the introducer sleeve. A similar "solution" to the leakage problem that is sometimes practiced in the art is to squeeze or pinch the exposed end of the introducer sleeve between the thumb and forefinger.

Neither of these methods for reducing the undesired flow of fluids and air through the introducer sleeve is deemed by the inventor to be acceptable. In both cases, at least one of the physician's hands is required, thereby making it difficult for the physician to attend to other or more important matters. Moreover, squeezing the exposed end of the introducer sheath can deform or even break the introducer at that point, making lead insertion difficult and increasing the danger of damage to the lead as it passes through the introducer.

In addition, neither placing the thumb over the end of the introducer, nor squeezing the end of the introducer, will be sufficiently effective in preventing the flow of blood and air in the introducer once a guide wire has been threaded through the introducer. Also, the configuration of the end of some types of introducer sheath is such that it is difficult or impossible to seal the end of the introducer shut with the thumb.

A tricuspid valve system for catheter (as opposed to lead) introducers is also deemed to be unacceptable for use in conjunction with lead introducers. The tricuspid valve arrangement for catheters could damage the sensitive lead tip of a placing lead. The application of pressure required to open the tricuspid valve can result in distortion or breakage of the lead tip. Moreover, some presently known tricuspid systems are lubricated with silicone-based oil. The electrical properties of pacing/sensing leads, and the chemical properties of steroid-eluting lead tips and the like, can be severely affected by coming in contact with the oil.

A valve for reducing undesired flow of fluids and air through an introducer sleeve is described in U.S. Pat. No. 5,441,504 (Pohndorf et al., issued Aug. 15, 1995) and assigned to Medtronic, Inc. Although the valve described in that patent is a substantial advance in the art, it nonetheless can prove troublesome during the dilation procedure for certain practitioners who may require the use of two hands in order to properly manipulate the valve and hold the introducer assembly at the same time. The present invention is directed to a solution for this problem and enables an introducer assembly and valve to be operated with a single hand while a lead is being inserted into a patient.

SUMMARY OF THE INVENTION

The invention is useful in an introducer for introducing a lead or catheter into a human patient. An introducer sheath having a hollow cylindrical body with a proximal end is configured to permit the introduction of lead or catheter. A tab is disposed at the proximal end that extends through the tab. The tab defines a first axis of rotation and a second axis of rotation. First and second handles are carried by the tab at opposing ends of the tab. A second link is rotatable about the first axis of rotation and couples the first valve member with the first handle. A second line is rotatable about the second axis of rotation and couples the second valve member with the second handle. A biasing assembly normally biases the valve members in their closed positions and enables the valve members to move to their open positions in response to a first force exerted on the first handle in a first direction and a second force exerted on the second handle in a second direction. Preferably, the first and second directions are opposite each other.

By using the foregoing techniques, an introducer and valve member can be operated with a single hand while a lead or catheter is being inserted into a patient. This substantially reduces the difficulty of the procedure for the practitioner.

BRIEF DESCRIPTION OF THE DRAWINGS

These and other advantages and features of the invention will become apparent upon reading the following detailed descriptions and referring to the accompanying drawings in which like numbers refer to like parts throughout and in which:

FIG. 2 is a top plan view of a preferred form of valve assembly made in accordance with the invention;

DESCRIPTION OF THE PREFERRED EMBODIMENTS

Figure 1:
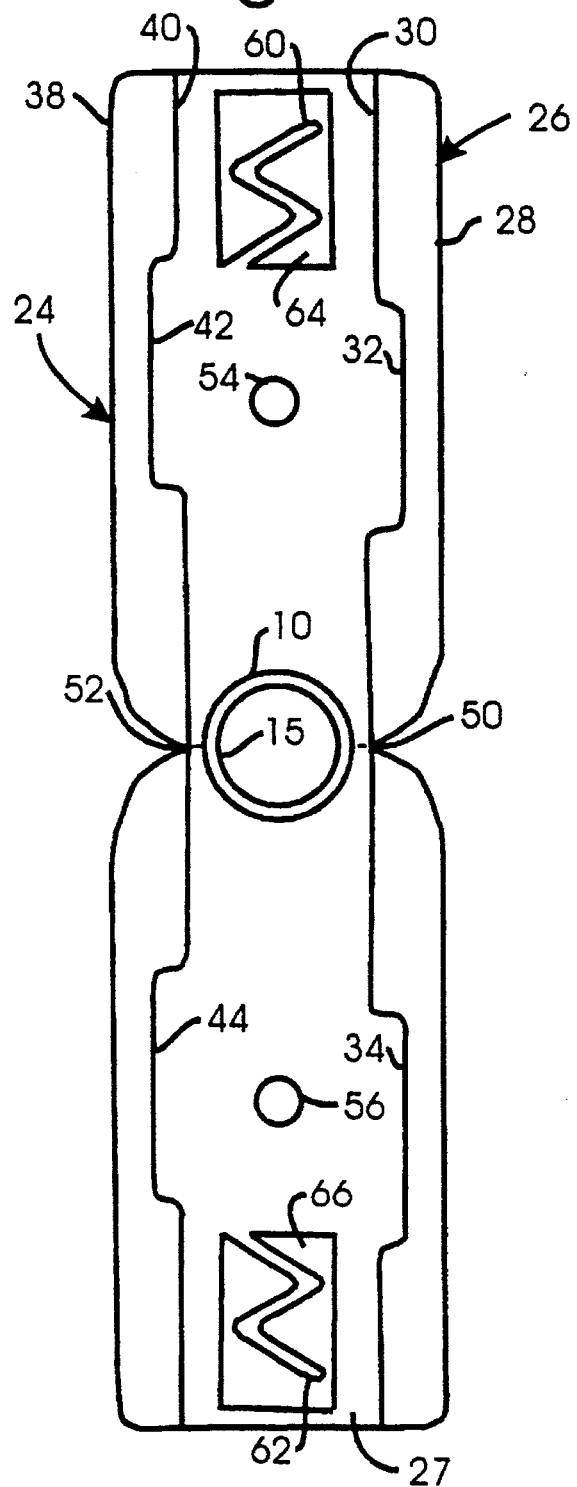
FIG. 1 is a top plan view of a preferred form of a tab for an introducer assembly made in accordance with the preferred practice of the present invention.
Figure 1A:
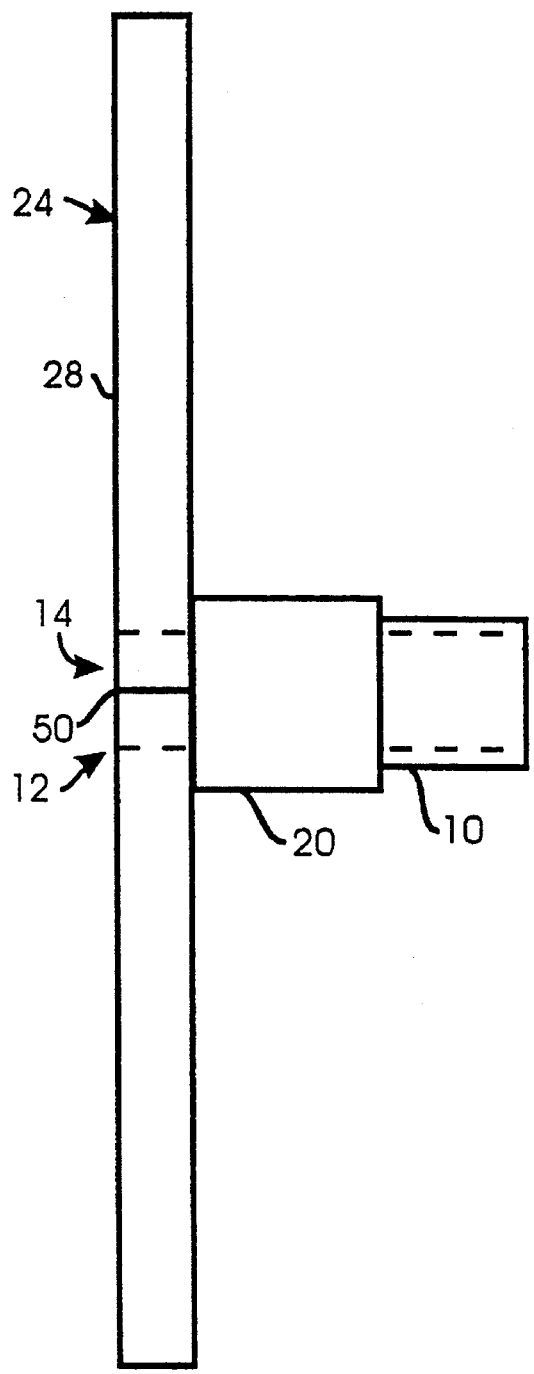
FIG. 1A is a side elevational view of the tab shown in FIG. 1.

Referring to FIGS. 1 and 1A, the preferred embodiments may be used in connection with a conventional introducer sheath 10 that is hollow and cylindrical. The sheath has a proximal end 12 with an opening 14 defined by an inner surface 15 of sheath 10. Introducer sheaths, like sheath 10, are well known in the art and are described, for example, in U.S. Pat. No. 5,441,504 ("the '504 Patent").

Sheath 10 may receive a vessel dilator, such as dilator 66 shown in FIG. 15 of the '504 Patent. Sheath 10 terminates in a support tube 20 that carries a tab 24. A related support and tab are shown in FIG. 15 and 16 of the '504 Patent.

Tab 24 includes a frame 26 having a side wall 28 that defines an inner edge 30 having cut out portions 32 and 34 as shown. Frame 26 also includes a side wall 38 defining an inner edge 40 that has cut out portions 42 and 44 as shown. A shelf 27 is formed by the bottom of frame 24.

Wall 28 tapers to define a tapered line 50, and wall 38 tapers to define a tapered line 52. Lines 50 and 52 form line of structural weakness that enable a practitioner to easily break away tab 24 during the surgical insertion of a lead or catheter. Liner of structural weakness 50 and 52 extend to the outer surface of sheath 10. The manner of breaking away the tab and the manner of introducing the lead or catheter are described in the '504 Patent, and therefore require no further explanation.

Tab 24 also defines cylindrical posts 54 and 56 having center lines that define axes of rotation. Tab 24 also includes biasing springs 60 and 62 that are integrally formed with the tab. The springs are cantilevered over cut out portions 64 and 66 that extend through the entire thickness of tab 24.

Referring to FIG. 2, a preferred form of valve assembly 80 made in accordance with the present invention basically comprises a valve member 82 that defines a comating valve surface 84. Assembly 80 also includes a handle 90 having a concave surface 92 adapted to be pushed by a finger or thumb and a depending lip 93.

Assembly 80 also includes a link assembly 100 that defines a center hole 102 adapted to fit over post 54 or 56 (FIG. 1). Link assembly 100 also includes link members 104 and 106 that are reversed from left to right, as well as an axle member 108 that defines center hole 102.

Flexible elbows 110–113 allow rotation of link assembly 100 as will be explained in connection with FIGS. 3 and 4. The elbows preferably are about 0.015 inch wide and 0.065 inch thick.

Valve assembly 80 is integrally molded from any conventional plastic such as polyethylene which may be transparent. Tab 24 is fabricated from a conventional plastic such as polyethylene.

Figure 3:
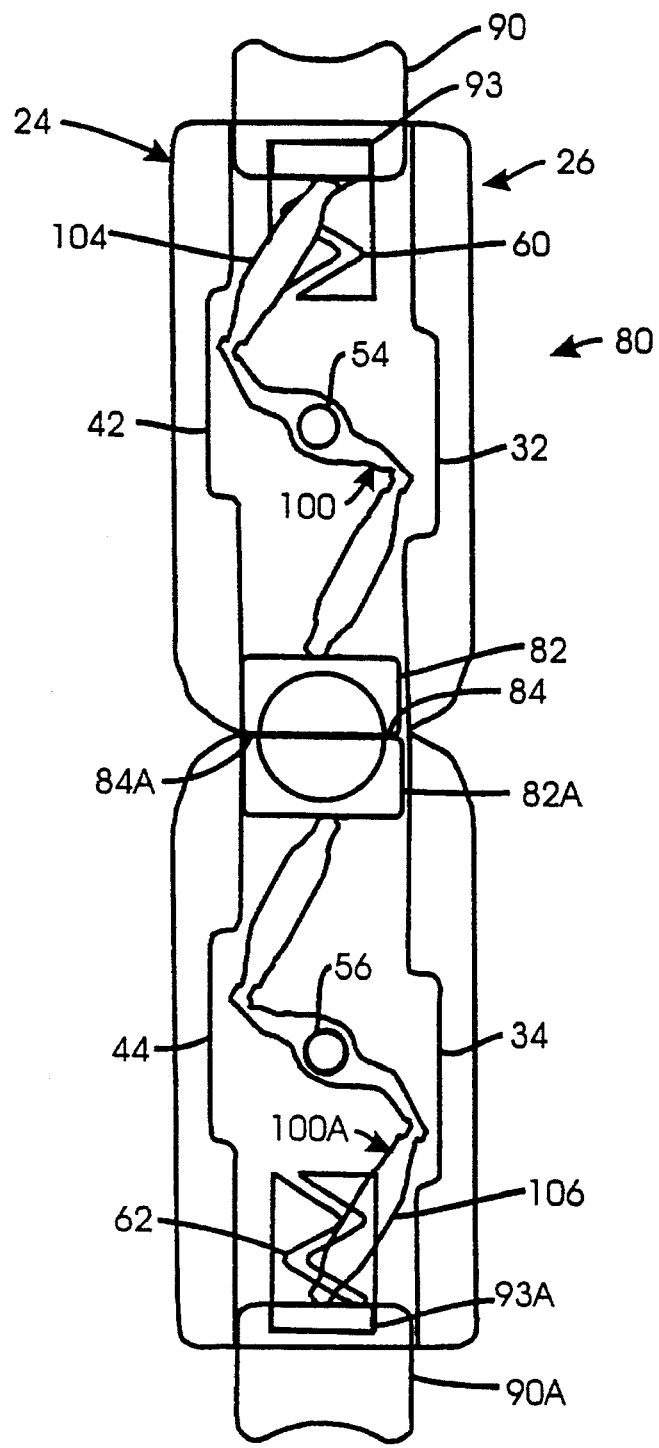
FIG. 3 is a top plan view of the valve assembly mounted on the tab in a closed position.
Figure 3A:
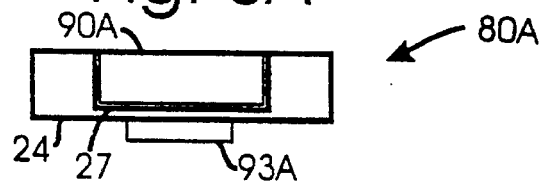
FIG. 3A is an end elevational view of the assemblies shown in FIG. 3 with parts removed for clarity.

FIG. 3 illustrates valve assembly 80 that has been mounted in tab 24 to slide on shelf 27. Also mounted on tab 24 is a valve assembly 80A that is identical to valve assembly 80 and has corresponding parts indicated by the letter "A". FIG. 3 illustrates valve assemblies 80 and 80A in a closed position wherein comating surfaces 84 and 84A are in abutting relationship to close opening 14. Valve assemblies 80 and 80A are held in the positions shown in FIG. 3 by springs 60 and 62 that press against lips 93 and 93A of handles 90 and 90A, respectively. That is, spring 60 exerts a force in an upward direction on handle 90 as shown in FIG. 3, and spring 62 exerts a force in a downward direction on handle 90A as shown in FIG. 3. Lip 93 extends through cut out area 64, and lip 93A extends through cut out area 66 (FIG. 3A).

In order to more clearly show the relationship between the springs and link assemblies, link member 104 is shown as an opaque part, and link member 106 is shown as a transparent part.

Figure 4:
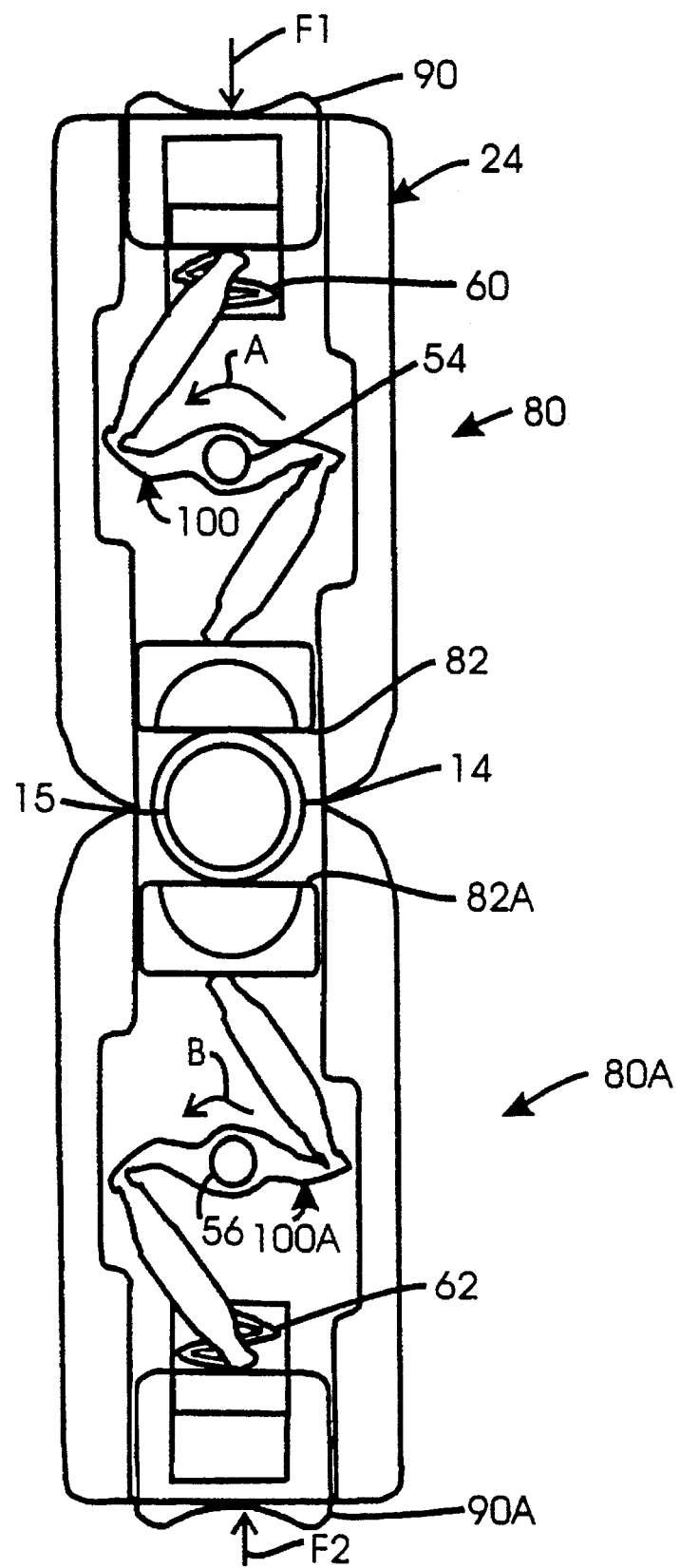
FIG. 4 is a view like FIG. 3 showing the valve assembly in an open position.

FIG. 4 illustrates valve assemblies 80 and 80A mounted on tab 24 in their open position. Valve assemblies 80 and 80A have been moved to the position shown in FIG. 4 by exerting a force F1 on handle 90 and a force F2 on handle 90A. As shown in FIG. 4, forces F1 and F2 are in opposite directions. The forces cause links 100 and 100A to rotate in directions A and B, respectively. Forces F1 and F2 cause spring 60 and 62 to compress as shown, thereby exerting force in directions opposite F1 and F2. As soon as handles 90 and 90A are released by the practitioner, springs 60 and 62 urge handles 90 and 90A in directions opposite F1 and F2 so that valve assemblies 80 and 80A resume the positions shown in FIG. 3.

Sufficient force to move assemblies 80 and 80A to their open positions can be exerted easily on handles 90 and 90A by a thumb and index finger of a single hand, since tab 24 is about 1.25 inches in length. As shown in FIG. 3 and 4, cut out portions 32, 34, 42 and 44 accommodate link assemblies 100 and 100A as they rotate. This is an important feature that improves structural strength and reduces material costs.

Flexible elbows 100–113 are important features that enable the link assemblies to be economically fabricated by molding and yet enable the valve assembly to be moved between opened and close positions in a reliable manner. This enables precise operation in a disposable part.

Those skilled in the art will recognize that the preferred embodiments may be altered or amended without departing from the true spirit and scope of the invention, as defined in the accompanying claims.

I claim:

1. An introducer for introducing a lead or catheter comprising:

an introducer sheath having a hollow cylindrical body with a proximal end configured to permit the introduction of said lead or catheter, said sheath defining an opening at said proximal end;

a tab disposed at said proximal end and extending radially outward from said proximal end, said tab defining a first axis of rotation and a second axis of rotation;

first and second comating valve members carried by said tab, said valve members being movable from a closed position covering said opening to an open position exposing said opening;

first and second handles carried by said tab at opposing ends of said tab;

a first link rotatable about said first axis of rotation for coupling said first valve member with said first handle;

a second link rotatable about said second axis of rotation for coupling said second valve member with said second handle;

bias means for normally biasing said valve members in said closed position and for enabling said valve members to move to said open position in response to a first force exerted on said first handle in a first direction and a second force exerted on said second handle in a second direction opposite said first direction, whereby said introducer and said valve members can be operated with a single hand while said lead or catheter is being inserted into a patient.

2. An introducer, as claimed in claim 1, wherein said first link enables said first valve member to move in said second direction in response to said first force exerted on said first handle in said first direction.

3. An introducer, as claimed in claim 2, wherein said second link enables said second valve member to move in said first direction in response to said second force exerted on said second handle in said second direction.

4. An introducer, as claimed in claim 1, wherein said first and second valve members have an abutting relationship in said closed position.

5. An introducer, as claimed in claim 1, wherein said tab comprises a frame with cut out sections to accommodate said first and second links.

6. An introducer, as claimed in claim 1, wherein said bias means is integrally formed with said tab.

7. An introducer, as claimed in claim 1, wherein said bias means and said tab are molded from plastic.

8. An introducer, as claimed in claim 1, wherein said bias means comprises a first spring that is compressed by said first handle in response to said first handle moving in said first direction and a second spring that is compressed by said second handle in response to said second handle moving in said second direction.

9. An introducer, as claimed in claim 1, wherein said first link and said second link rotate in the same direction.

* * * * *